United States Patent [19]

Fischer, deceased et al.

[11] 4,219,493
[45] Aug. 26, 1980

[54] SUBSTITUTED O-ALKYLSULFONYLGLYCOLIC ACID ANILIDES

[75] Inventors: Adolf Fischer, deceased, late of Mutterstadt, Fed. Rep. of Germany, by Caecilia Emma Fischer, heiress-at-law; Wolfgang Rohr, Mannheim; Gerhard Paul, Ludwigshafen, both of Fed. Rep. of Germany

[73] Assignee: BASF Aktiengesellschaft, Fed. Rep. of Germany

[21] Appl. No.: 974,620

[22] Filed: Dec. 27, 1978

Related U.S. Application Data

[63] Continuation of Ser. No. 638,957, Dec. 8, 1975, abandoned.

[30] Foreign Application Priority Data

Dec. 13, 1974 [DE] Fed. Rep. of Germany ....... 2458972

[51] Int. Cl.$^2$ ............................................. C07C 143/68
[52] U.S. Cl. .................................. 260/456 A; 71/103
[58] Field of Search ..................................... 260/456 A

[56] References Cited

U.S. PATENT DOCUMENTS

| | | | |
|---|---|---|---|
| 3,536,721 | 10/1970 | Soong et al. ...................... | 260/456 A |
| 3,849,467 | 11/1974 | Mangold et al. ................ | 260/456 A |
| 3,865,860 | 2/1975 | Rohr et al. ....................... | 260/456 A |
| 3,870,740 | 3/1975 | Fischer et al. ................... | 260/456 A |
| 4,025,544 | 5/1977 | Fischer et al. ................... | 260/456 A |

*Primary Examiner*—Nicky Chan
*Attorney, Agent, or Firm*—Keil & Witherspoon

[57] ABSTRACT

New and valuable O-substituted glycolic acid anilides having a good herbicidal action, a process for their manufacture, herbicides containing these new compounds as active ingredients, and a process for controlling the growth of unwanted plants with these active ingredients.

8 Claims, No Drawings

SUBSTITUTED O-ALKYLSULFONYLGLYCOLIC ACID ANILIDES

This is a continuation of application Ser. No. 638,957, filed Dec. 8, 1975, now abandoned.

The present invention relates to new and valuable O-substituted glycolic acid anilides having a good herbicidal action, a process for their manufacture, herbicides containing these new compounds as active ingredients, and a process for selective weed control in crops with the new active ingredients or agents containing them.

It is known (German Laid-Open Application DOS 2,160,380) to use O-alkylsulfonylglycolic acid anilides, particularly O-methylsulfonylglycolic acid-(N-sec-butyl)-anilide, as herbicides. However, their herbicidal action is poor.

It is an object of the present invention to provide O-substituted glycolic acid anilides having superior plant-influencing properties and which at low application rates combat a larger number of weed species, and particularly very resistant weeds, much better than the prior art O-substituted glycolic acid anilides without causing damage to crop plants.

We have now found that substituted O-alkylsulfonylglycolic acid anilides of the formula

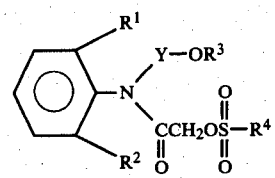

where $R^1$ denotes hydrogen, methyl, ethyl, n-propyl or isopropyl, $R^2$ denotes methyl, ethyl, n-propyl or isopropyl, $R^3$ denotes alkyl of a maximum of 3 carbon atoms, alkenyl of 3 or 4 carbon atoms, cyclopropyl or cyclopropylmethyl, Y denotes an unsubstituted ethylene chain (—CH$_2$—CH$_2$—) or an ethylene chain monosubstituted by ethyl or having one or two methyl substituents, and $R^4$ denotes lower, optionally halogen-substituted, alkyl of a maximum of 4 carbon atoms (methyl, ethyl, chloroethyl, chloromethyl, propyl, isopropyl, butyl, isobutyl, sec-butyl), have a better herbicidal action than the prior art compounds.

The superior action of the new O-substituted glycolic acid anilides according to the invention is atttibutable to the fact that their chemical structure deviates basically from that of the prior art compounds.

The new O-substituted glycolic acid anilides of the formula I are prepared in accordance with the invention by reacting an N-substituted glycolic acid anilide of the formula

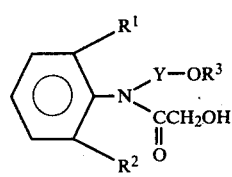

with a sulfonyl halide of the formula

in the presence of an acid-binding agent. In formulae II and III, $R^1$, $R^2$, $R^3$, Y and $R^4$ have the meanings given at formula I. Hal denotes a halogen atom.

The reaction may be carried out in the presence or absence of solvents or diluents which are inert to the reactants, e.g., aliphatic, aromatic or halogenated hydrocarbons, such as benzene, toluene, xylenes, petroleum ether, chlorobenzene, methylene chloride, 1,2-dichloroethane and chloroform; ethers and ethereal compounds, such as dialkyl ether, dioxane and tetrahydrofuran; nitriles, such as acetonitrile; N,N-dialkylated amides, such as dimethylformamide, and mixtures of these solvents.

Preferred sulfonyl halides are the acid chlorides of methanesulfonic acid, ethanesulfonic acid, propanesulfonic acid, isopropanesulfonic acid, chloromethanesulfonic acid and chloroethanesulfonic acid.

The reaction is carried out at a temperature of from −30° to +100° C., preferably from −5° to +30° C., in the presence of an acid-binding agent. Suitable acid-binding agents are tertiary amines, such as trialkylamines, e.g., triethylamine, pyridine and pyridine bases, and inorganic bases, such as the oxides, hydroxides, hydrogen carbonates and carbonates of alkali and alkaline earth metals.

The starting materials of the formula II are new; they may be prepared by known methods, e.g., by reaction of N-substituted anilines of the formula

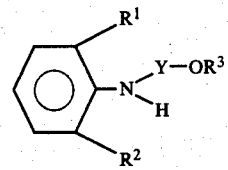

with acetoxyacetyl chloride to give the corresponding acetoxy-acetanilide of the formula

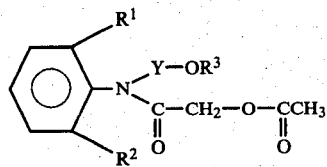

followed by elimination of the acyl radical by hydrolysis or transesterification to give a glycolic acid anilide of the formula

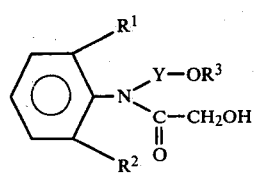

The starting materials of the formula IV are known, e.g., from German Laid-Open Applications DOS 2,305,495 and DOS 2,328,340.

Some of the compounds according to the invention of the formula I may be prepared in a single stage process by reaction of N-substituted anilines of the formula IV with an O-substituted glycolic acid halide of the formula

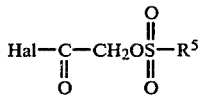      VII in the presence of an acid-binding agent; $R^5$ denotes alkyl, especially methyl and ethyl. Starting materials of the formula VII are disclosed in U.S. Pat. No. 3,200,138.

The preparation of the compounds of the invention is illustrated by the following examples.

EXAMPLE 1

(a) 2,6-dimethyl-N-1-(methoxyprop-2-yl)-acetoxyacetanilide

At 0° to +5° C. and while stirring, a mixture of 152 parts by weight of 2,6-dimethyl-N-(1-methoxyprop-2-yl)-aniline, 79.5 parts by weight of triethylamine and 220 parts by weight of toluene was added at a rate depending on the heat of reaction to a solution of 107.5 parts by weight of acetoxyacetyl chloride in 500 parts by weight of toluene. When the reaction was over, the mixture was extracted with water, dilute hydrochloric acid and dilute sodium bicarbonate solution. The organic phase was dried with magnesium sulfate and freed from solvent in vacuo. The crude product obtained was used without further purification in the following reaction.

(b) 2,6-dimethyl-N-(1-methoxypro-2-yl)-glycolic acid anilide 183 parts by weight of the crude 2,6-dimethyl-N-(1-methoxyprop-2-yl)-acetoxyacetanilide was dissolved in a mixture of 240 parts by weight of water and 800 parts by weight of methanol; the whole was then hydrolyzed at 40° to 45° C. by the addition of a solution of 36.6 parts by weight of potassium hydroxide in 310 parts by weight of methanol.

The reaction mixture was worked up by substantially freeing it from solvent and extracting the reaction product with dichloromethane.

Upon concentration of the dried dichloromethane solution a crystalline crude product was obtained which was further purified by recrystallization from diethyl ether; m.p.: 77° to 78° C.

The compound has the following structural formula:

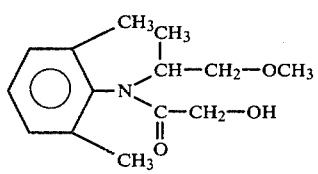

(c) 2,6-dimethyl-N-(1-methoxyprop-2-yl)-O-methylsulfonyloxy-glycolic acid anilide At 0° to +5° C. a solution of 13.7 parts by weight of methane sulfochloride in 26 parts by weight of dichloromethane was added to a solution of 25.1 parts by weight of 2,6-dimethyl-N-(1-methoxyprop-2-yl)-glycolic acid anilide and 13.2 parts by weight of triethylamine in 130 parts by weight of dichloromethane. The reaction mixture was worked up by treatment with water, dilute hydrochloric acid and dilute sodium bicarbonate solution. The dichloromethane solution was dried with magnesium sulfate and concentrated, the crude product being obtained as crystals. After recrystallization from diisopropyl ether the analytically pure substance melts at 77° C.

The compound has the following structural formula:

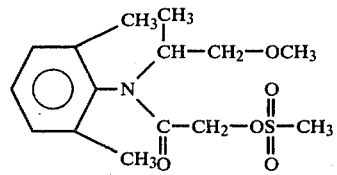

EXAMPLE 2

2-methyl-6-ethyl-N-(1-methoxyprop-2-yl)-O-methylsulfonyloxy glycolic acid anilide At 0° to +5° C. a solution of 207 parts by weight of 2-methyl-6-ethyl-N-(1-methoxyprop-2-yl)-aniline and 122 parts by weight of triethylamine in 450 parts by weight of tetrahydrofuran was added to a solution of 190 parts by weight of O-methylsulfonylglycolic acid chloride in 450 parts by weight of tetrahydrofuran. The mixture was afterreacted for 1 hour by stirring it at room temperature (20° C.). Subsequently the hydrochloride was separated and the filtrate concentrated in vacuo. The oily residue was dissolved in ethyl acetate and extracted with water, dilute hydrochloric acid and dilute sodium bicarbonate solution. The organic phase was dried with magnesium sulfate, treated with activated carbon and silica gel, and subsequently concentrated in vacuo.

The oil which remained ($n_D^{25}$:1.5170) did not crystallize out even after standing for a fairly long period of time.

The spectroscopic data and the ultimate analysis results agree with the following structure:

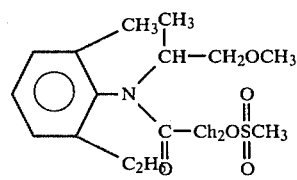

The following compounds were prepared in accordance with the procedure described in the foregoing examples:

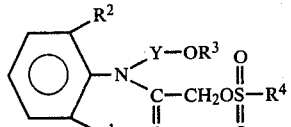

| $R^2$ | $R^1$ | Y | $R^3$ | $R^4$ | |
|---|---|---|---|---|---|
| $CH_3$ | $CH_3$ | $-CH(CH_3)CH_2-$ | $CH_3$ | $C_2H_5$ | $n_D^{25}$ 1.5161 |
| $CH_3$ | $C_2H_5$ | $-CH(CH_3)CH_2-$ | $CH_3$ | $C_2H_5$ | $n_D^{25}$ 1.5120 |
| $CH_3$ | $CH_3$ | $-CH(CH_3)CH_2-$ | $CH_3$ | $C_3H_7$ | |
| $CH_3$ | $C_2H_5$ | $-CH(CH_3)CH_2-$ | $CH_3$ | $C_3H_7$ | $n_D^{25}$ 1.5110 |
| $CH_3$ | $CH_3$ | $-CH(CH_3)CH_2-$ | $CH_3$ | $i$-$C_3H_7$ | |
| $CH_3$ | $C_2H_5$ | $-CH(CH_3)CH_2-$ | $CH_3$ | $i$-$C_3H_7$ | $n_D^{25}$ 1.5110 |
| $C_2H_5$ | $C_2H_5$ | $-CH(CH_3)CH_2-$ | $CH_3$ | $CH_3$ | $n_D^{18}$ 1.5189 |
| $C_2H_5$ | $C_2H_5$ | $-CH(CH_3)CH_2-$ | $CH_3$ | $C_2H_5$ | |
| $C_2H_5$ | $C_2H_5$ | $-CH(CH_3)CH_2-$ | $CH_3$ | $C_3H_7$ | |
| $C_2H_5$ | $C_2H_5$ | $-CH(CH_3)CH_2-$ | $CH_3$ | $i$-$C_3H_7$ | |
| $CH_3$ | H | $-CH(CH_3)CH_2-$ | $CH_3$ | $CH_3$ | |
| $CH_3$ | H | $-CH(CH_3)CH_2-$ | $CH_3$ | $C_2H_5$ | |
| $CH_3$ | H | $-CH(CH_3)CH_2-$ | $CH_3$ | $C_3H_7$ | |
| $CH_3$ | H | $-CH(CH_3)CH_2-$ | $CH_3$ | $i$-$C_3H_7$ | |
| $C_2H_5$ | H | $-CH(CH_3)CH_2-$ | $CH_3$ | $CH_3$ | $n_D^{25}$ 1.5170 |
| $C_2H_5$ | H | $-CH(CH_3)CH_2-$ | $CH_3$ | $C_2H_5$ | $n_D^{25}$ 1.5140 |
| $C_2H_5$ | H | $-CH(CH_3)CH_2-$ | $CH_3$ | $C_3H_7$ | |
| $C_2H_5$ | H | $-CH(CH_3)CH_2-$ | $CH_3$ | $i$-$C_3H_7$ | |
| $CH_3$ | $CH_3$ | $-CH_2CH_2-$ | $CH_3$ | $CH_3$ | |
| $CH_3$ | $C_2H_5$ | $-CH_2CH_2-$ | $CH_3$ | $CH_3$ | $n_D^{25}$ 1.5185 |
| $C_2H_5$ | $C_2H_5$ | $-CH_2CH_2-$ | $CH_3$ | $CH_3$ | |
| $CH_3$ | $CH_3$ | $-CH_2CH_2-$ | $C_2H_5$ | $CH_3$ | |
| $CH_3$ | $CH_3$ | $-CH_2CH_2-$ | $i$-$C_3H_7$ | $CH_3$ | |
| $CH_3$ | $CH_3$ | $-CH_2CH_2-$ | $-CH_2CH=CH_2$ | $CH_3$ | |
| $CH_3$ | H | $-CH_2CH_2-$ | $CH_3$ | $CH_3$ | |
| $i$-$C_3H_7$ | H | $-CH_2CH_2-$ | $CH_3$ | $CH_3$ | |
| $C_2H_5$ | H | $-CH_2CH_2-$ | $CH_3$ | $CH_3$ | |
| $CH_3$ | $CH_3$ | $-CH(CH_3)CH_2-$ | $C_2H_5$ | $CH_3$ | |
| $CH_3$ | $C_2H_5$ | $-CH(CH_3)CH_2-$ | $C_2H_5$ | $CH_3$ | |
| $C_2H_5$ | $C_2H_5$ | $-CH(CH_3)CH_2-$ | $C_2H_5$ | $CH_3$ | |
| $CH_3$ | $CH_3$ | $-CH_2CH(CH_3)-$ | $CH_3$ | $CH_3$ | |
| $C_2H_5$ | $CH_3$ | $-CH_2CH(CH_3)-$ | $CH_3$ | $CH_3$ | |
| $C_2H_5$ | $C_2H_5$ | $-CH_2CH(CH_3)-$ | $CH_3$ | $CH_3$ | |
| $CH_3$ | $CH_3$ | $-CH(CH_3)CH_2-$ | $CH_3$ | $CH_2Cl$ | |
| $CH_3$ | $C_2H_5$ | $-CH(CH_3)CH_2-$ | $CH_3$ | $CH_2Cl$ | |
| $C_2H_5$ | $C_2H_5$ | $-CH(CH_3)CH_2-$ | $CH_3$ | $CH_2Cl$ | |
| $CH_3$ | $CH_3$ | $-CH(CH_3)CH_2-$ | $C_2H_5$ | $CH_2Cl$ | |
| $C_2H_5$ | $CH_3$ | $-CH(CH_3)CH_2-$ | $C_2H_5$ | $CH_2Cl$ | |
| $C_2H_5$ | $C_2H_5$ | $-CH(CH_3)CH_2-$ | $C_3H_7$ | $CH_2Cl$ | |
| $CH_3$ | $C_2H_5$ | $-CH_2-CH_2$ | $CH_3$ | $C_2H_5$ | $n_D^{25}$ 1.5135 |

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol ester, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tank-mix)) oils of various types, herbicides, fungicides, nematocides, insecticides, bactericides, trace elements, fertilizers, antifoams (e.g., silicones), growth regulators, antidotes and other herbicidally effective compounds such as
substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance

| | |
|---|---|
| Gramineae, such as | |
| Cynodon spp. | Dactylis spp. |
| Digitaria spp. | Avena spp. |
| Echinochloa spp. | Bromus spp. |
| Setaria spp. | Uniola spp. |
| Panicum spp. | Poa spp. |
| Alopecurus spp. | Leptochloa spp. |
| Lolium spp. | Brachiaria spp. |
| Sorghum spp. | Eleusine spp. |
| Agropyron spp. | Cenchrus spp. |
| Phalaris spp. | Eragrotis spp. |
| Apera spp. | *Phragmites communis* |
| etc.; | |
| Cyperaceae, such as | |
| Carex spp. | Eleocharis spp. |
| Cyperus spp. | Scirpus spp. |
| etc.; | |
| dicotyledonous weeds, such as | |
| Malvaceae, e.g., | |
| *Abutilon theoprasti* | Hibiscus spp. |
| Sida spp. | Malva spp. |
| etc.; | |
| Compositae, such as | |
| Ambrosia spp. | Centaurea spp. |
| Lactuca spp. | Tussilago spp. |
| Senecio spp. | *Lapsana communis* |
| Sonchus spp. | Tagetes spp. |
| Xanthium spp. | Erigeron spp. |
| Iva spp. | Anthemis spp. |
| Galinsoga spp. | Matricaria spp. |
| Taraxacum spp. | Artemisia spp. |
| Chrysanthemum spp. | Bidens spp. |
| Cirsium spp. | etc.; |
| Convolvulaceae, such as | |
| Convolvulus spp. | Cuscuta spp. |
| Ipomoea spp. | *Jaquemontia tamnifolia* |
| etc.; | |
| Cruciferae, such as | |
| *Barbarea vulgaris* | *Arabidopsis thaliana* |
| Brassica spp. | Descurainia spp. |
| Capsella spp. | Draba spp. |
| Sisymbrium spp. | *Coronopus didymus* |
| Thlaspi spp. | Ledidium spp. |
| *Sinapis arvensis* | Raphanus spp. |
| etc.; | |
| Geraniaceae, such as | |
| Erodium spp. | Geranium spp. |
| etc.; | |
| Portulacaceae, such as | |
| Portulaca spp. | etc.; |
| Primulaceae, such as | |
| *Anagallis arvensis* | Lysimachia spp. |
| etc.; | |
| Rubiaceae, such as | |
| Richardia spp. | Diodia spp. |
| Galium spp. | etc.; |
| Scrophulariaceae, such as | |
| Linaria spp. | Digitalis spp. |
| Veronica spp. | etc.; |
| Solanaceae, such as | |
| Physalis spp. | Nicandra spp. |
| Solanum spp. | Datura spp. |
| etc.; | |
| Urticaceae, such as | |
| Urtica spp. | |
| Violaceae, such as | |
| Viola spp. | etc.; |
| Zygophyllaceae, such as | |

-continued

| | |
|---|---|
| *Tribulus terrestris* | etc.; |
| Euphorbiaceae, such as | |
| *Mercurialis annua* | Euphorbia spp. |
| Umbelliferae, such as | |
| *Daucus carota* | Ammi majus |
| Aethusa cynapium | etc.; |
| Commelinaceae, such as | |
| Commelina spp. | etc.; |
| Labiatae, such as | |
| Lamium spp. | Galeopsis spp. |
| etc.; | |
| Leguminosae, such as | |
| Medicago spp. | *Sesbania exaltata* |
| Trifolium spp. | Cassia spp. |
| Vicia spp. | Lathyrus spp. |
| etc.; | |
| Plantaginaceae, such as | |
| Plantago spp. | etc.; |
| Polygonaceae, such as | |
| Polygonum spp. | Fagopyrum spp. |
| Rumex spp. | etc.; |
| Aizoaceae, such as | |
| Mollugo verticillata | etc.; |
| Amaranthaceae, such as | |
| Amaranthus spp. | etc.; |
| Boraginaceae, such as | |
| Amsinckia spp. | Anchusa spp. |
| Myostis spp. | Lithospermum spp. |
| etc.; | |
| Caryophyllaceae, such as | |
| Stellaria spp. | Silene spp. |
| Spergula spp. | Cerastium spp. |
| Saponaria spp. | *Agrostemma githago* |
| Scleranthus annus | etc.; |
| Chenopodiaceae, such as | |
| Chenopodium spp. | Atriplex spp. |
| Kochia spp. | *Monolepsis nuttalliana* |
| Salsola Kali | etc.; |
| Lythraceae, such as | |
| Cuphea spp. | etc.; |
| Oxalidaceae, such as | |
| Oxalis spp. | |
| Ranunculaceae, such as | |
| Ranunculus spp. | Adonis spp. |
| Delphinium spp. | etc.; |
| Papaveraceae, such as | |
| Papaver spp. | *Fumaria officinalis* |
| etc.; | |
| Onagraceae, such as | |
| Jussiaea spp. | etc.; |
| Rosaceae, such as | |
| Alchemillia spp. | Potentilla spp. |
| etc.; | |
| Potamogetonaceae, such as | |
| Potamogeton spp. | etc.; |
| Najadaceae, such as | |
| Najas spp. | etc.; |
| Equisetaceae | |
| Equisetum spp. | etc.; |
| Marsileaceae, such as | |
| *Marsilea quadrifolia* | etc.; |
| Polypodiaceae, | |
| *Pteridium quilinum* | |
| Alismataceae, such as | |
| Alisma spp. | *Sagittaria sagittifolia* |
| etc. | |

The herbicides according to the invention may be employed in cereal crops such as

| | |
|---|---|
| Avena spp. | Sorghum |
| Triticum spp. | Zea mays |
| Hordeum spp. | *Panicum miliaceum* |
| Secale spp. | Oryza spp. |
| *Saccharum offinicarum* | | and in dicotyledon crops such as

Crucifereae, e.g.
Brassica spp.    Raphanus spp.
Sinapis spp.     Lepidium spp.
Compositae, e.g.
Lactuca spp.     Carthamus spp.
Helianthus spp.  Scorzonera spp.
Malvaceae, e.g.
*Gossypium hirsutum*
Leguminosae, e.g.
Medicago spp.    Phaseolus spp.
Trifolium spp.   Arachis spp.
Pisum spp.       Glycine max.
Chenopodiaceae, e.g.
*Beta vulgaris*
Spinacia spp.
Solanaceae, e.g.
Solanum spp.     *Capsicum annuum*
Nicotiania spp.
Linaceae, e.g.
Linum spp.
Umbelliferae, e.g.
Petroselinum spp.  *Apium graveolens*
*Daucus carota*
Rosaceae, e.g.    Fragaria
Cucurbitaceae, e.g.
Cucumis spp.      Cucurbita spp.
Liliaceae, e.g.
Allium spp.
Vitaceae, e.g.
*Vitis vinifera*
Bromeliaceae, e.g.
Ananas sativus.

EXAMPLE 3

In the greenhouse, loamy sandy soil was filled into pots and sown with the seeds of various plants. The soil was then immediately treated with 0.8 kg/ha of each of the following active ingredients, each being dispersed or emulsified in 500 liters of water per hectare:

I   2,6-diethyl-N-(1-methoxyprop-2-yl)-O-methylsulfonylglycolic acid anilide

II  2,6-dimethyl-N-(1-methoxyprop-2-yl)-O-ethylsulfonylglycolic acid anilide

III 2,6-dimethyl-N-(1-methoxyprop-2-yl)-O-methylsulfonylglycolic acid anilide and for comparison, IV  O-methylsulfonylglycolic acid-N-sec-butylanilide After 4 to 5 weeks it was ascertained that active ingredients I, II and III had a better herbicidal action than compound IV, combined with the same crop tolerance.

The results are given below:

| Active ingredient kg/ha | I 0.8 | II 0.8 | III 0.8 | IV 0.8 |
|---|---|---|---|---|
| Crop plants: | | | | |
| Gossypium hirsutum | 0 | 0 | 0 | 0 |
| Zea Mays | 0 | 0 | 0 | 0 |
| Glycine max. | 0 | 0 | 0 | 0 |
| Oryza sativa | 0 | 0 | 0 | 0 |
| Brassica spp. | 0 | 0 | 0 | 0 |
| Beta vulgaris | 0 | 0 | 0 | 0 |
| Unwanted plants: | | | | |
| Echinochloa crus-galli | 75 | 85 | 90 | 30 |
| Digitaria sanguinalis | 80 | 90 | 80 | 60 |

0 = no damage
100 = complete destruction

EXAMPLE 4

In the greenhouse, various plants were treated at a growth height of from 2 to 18 cm with 0.8 kg/ha of each of active ingredients I, II and III and comparative agent IV, each being dispersed or emulsified in 500 liters of water per hectare.

After 2 to 3 weeks it was ascertained that active ingredients I, II and III provided better weed control than IV, combined with the same crop plant compatibility.

The results are given below:

| Active ingredient ka/ha | I 0.8 | II 0.8 | III 0.8 | IV 0.8 |
|---|---|---|---|---|
| Crop plants: | | | | |
| Gossypium hirsutum | 0 | 0 | 0 | 0 |
| Zea mays | 0 | 0 | 0 | 0 |
| Glycine max. | 0 | 0 | 0 | 0 |
| Brassica spp. | 10 | 10 | 10 | 0 |
| Unwanted plants | | | | |
| Echinochloa crus-galli | 80 | 95 | 90 | 30 |

0 = no damage
100 = complete destruction

EXAMPLE 5

In the greenhouse, loamy sandy soil was filled into pots and sown with the seeds of various plants. The soil was then immediately treated with 3 kg/ha of each of the following active ingredients, each being dispersed or emulsified in 500 liters of water per hectare:

I.   2,6-diethyl-N-(1-methoxyprop-2-yl)-O-methylsulfonylglycolic acid anilide

II.  2,6-dimethyl-N-(1-methoxyprop-2-yl)-O-ethylsulfonylglycolic acid anilide

III. 2,6-dimethyl-N-(1-methoxyprop-2-yl)-O-methylsulfonylglycolic acid anilide

V.   2-methyl-6-ethyl-N-(1-methoxyprop-2-yl)-O-ethylsulfonylglycolic acid anilide VI.  2-methyl-6-ethyl-N-(1-methoxyprop-2-yl)-O-isopropylsulfonylglycolic acid anilide VII. 2-methyl-6-ethyl-N-(1-methoxyprop-2-yl)-O-methylsulfonylglycolic acid anilide.

After 4 to 5 weeks it was ascertained that the active ingredients had a strong herbicidal action and were well tolerated by the crop plants.

The results are given below:

| Active ingredient kg/ha | I 3 | II 3 | III 3 | V 3 | VI 3 | VII 3 |
|---|---|---|---|---|---|---|
| Crop plants: | | | | | | |
| Gossypium hirsutum | 10 | 10 | 0 | 0 | 0 | 0 |
| Glycine max. | 0 | 0 | 0 | 0 | 0 | 0 |
| Zea mays | 0 | 0 | 0 | 0 | 0 | 0 |
| Unwanted plants | | | | | | |
| Echinochloa crus-galli | 100 | 100 | 100 | 100 | 100 | 100 |
| Lolium multiflorum | 100 | 100 | 100 | 100 | 100 | 100 |

0 = no damage
100 = complete destruction

EXAMPLE 6

In the greenhouse, various plants were treated at a growth height of from 2 to 18 cm with 3 kg/ha of each of active ingredients I, II, III, V, VI and VII, each being dispersed or emulsified in 500 liters of water per hectare.

After 2 to 3 weeks it was ascertained that the active ingredients had a strong herbicidal action and were well tolerated by the crop plants.

The results are given below:

| Active ingredient kg/ha | I 3 | II 3 | III 3 | V 3 | VI 3 | VII 3 |
|---|---|---|---|---|---|---|
| Crop plants: | | | | | | |
| Gossypium hirsutum | 0 | 0 | 0 | 0 | 0 | 0 |
| Zea mays | 0 | 0 | 0 | 0 | 0 | 0 |
| Glycine max. | 0 | 0 | 0 | 0 | 0 | 0 |
| Unwanted plants: | | | | | | |
| Echinochloa crus-galli | 100 | 90 | 70 | 90 | 95 | 100 |
| Lolium multiflorum | 80 | 90 | 80 | 90 | 85 | 100 |

0 = no damage
100 = complete destruction

EXAMPLE 7

90 parts by weight of compound I is mixed with 10 parts by weight of N-methyl-α-pyrrolidone. A mixture is obtained which is suitable for application in the form of very fine drops.

EXAMPLE 8

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound III is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound I is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of caster oil. By pouring the solution into 100,000 parts by weight of water and uniformly distributing it therein, an aqueous dispersion is obtained containing 0.02% by weight of the active ingredient.

EXAMPLE 11

20 parts by weight of compound I is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound II is intimately mixed with 97 parts by weight of particulate kaolin. A dust is obtained containing 3% by weight of the active ingredient.

EXAMPLE 13

30 parts by weight of compound II is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

In the greenhouse the compounds

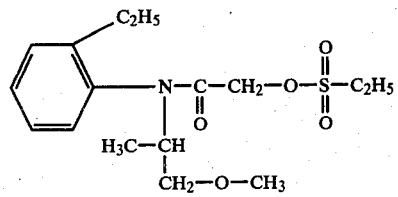

I and

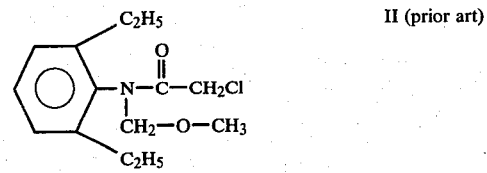

II (prior art)

were compared in the following experiments. Various crop plants and unwanted grasses were sown, separated by species, into pots filled with loamy sand soil. The soil was then immediately treated with the active ingredients, each being dispersed or emulsified in 500 liters of water per hectare. During the experiment the pots were kept thoroughly moist.

The individual plant species, the amounts of active ingredient and their action are apparent from the following table.

It was ascertained that the action of I is similar to that of II on unwanted grasses. The selectivity of I is however far better than that of II in cereals. As no damage is caused to white mustard, active ingredient I may be used in broad-leaved crops.

| Active ingredient kg/ha | I 0.5 | I 1.0 | I 2.0 | I 3.0 | II (prior art) 0.5 | II (prior art) 1.0 | II (prior art) 2.0 | II (prior art) 3.0 |
|---|---|---|---|---|---|---|---|---|
| Avena sativa (oats) | — | — | — | 0 | — | 57 | 67 | — |
| Triticum aestivum (wheat) | 0 | 0 | 0 | 30 | 36 | 54 | 74 | 68 |
| Sinapis alba (white mustard) | 0 | 0 | 0 | — | 25 | 45 | 60 | 70 |
| Alopecurus myosuroides | 40 | 40 | 80 | — | 65 | 85 | 95 | — |
| Echinochloa crus-galli | 100 | 100 | 100 | 100 | 89 | 99 | 100 | 100 |
| Lolium multiflorum | — | — | — | 100 | 83 | 98 | 100 | — |

0 = no damage
100 = complete destruction

We claim:
1. A substituted O-alkylsulfonylglycolic acid anilide of the formula

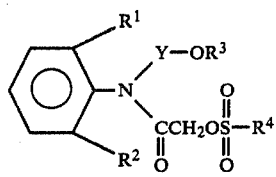

where $R^1$ denotes hydrogen, methyl, ethyl, n-propyl or isopropyl, $R^2$ denotes methyl, ethyl, n-propyl or isopropyl, $R^3$ denotes alkyl of a maximum of 3 carbon atoms, alkenyl of 3 or 4 carbon atoms, cyclopropyl or cyclopropylmethyl, Y denotes an ethylene chain monosubstituted by ethyl or having one or two methyl substituents, and $R^4$ denotes lower alkyl of a maximum of 4 carbon atoms or halogen-substituted alkyl of a maximum of 4 carbon atoms.

2. 2,6-dimethyl-N-(1-methoxyprop-2-yl)-O-methylsulfonylglycolic acid anilide.
3. 2,6-dimethyl-N-(1,methoxyprop-2-yl)-O-ethylsulfonylglycolic acid anilide.
4. 2,6-diethyl-N-(1-methoxyprop-2-yl)-O-methylsulfonylglycolic acid anilide.
5. 2-methyl-6-ethyl-N-(1-methoxyprop-2-yl)-O-methylsulfonylglycolic acid anilide.
6. 2-methyl-6-ethyl-N-(1-methoxyprop-2-yl)-O-ethylsulfonylglycolic acid anilide.
7. 2-methyl-6-ethyl-N-(1-methoxyprop-2-yl)-O-isopropylsulfonylglycolic acid anilide.
8. 2-ethyl-N-(1-methoxyprop-2-yl)-O-ethylsulfonylglycolic acid anilide.

* * * * *